United States Patent
Benedetto et al.

[11] Patent Number: 5,859,705
[45] Date of Patent: Jan. 12, 1999

[54] APPARATUS AND METHOD FOR USING LIGHT SCATTERING TO DETERMINE THE SIZE OF PARTICLES VIRTUALLY INDEPENDENT OF REFRACTIVE INDEX

[75] Inventors: Elizabeth E. Benedetto; John W. Lyons; Stewart P. Wood, all of Midland, Mich.

[73] Assignee: The Dow Chemical Company, Midland, Mich.

[21] Appl. No.: 67,307

[22] Filed: May 26, 1993

[51] Int. Cl.$^6$ .................................................. G01N 15/02
[52] U.S. Cl. ............................................. 356/336; 356/338
[58] Field of Search .............................. 356/335, 39, 336, 356/337, 338, 339, 340, 341, 342, 343; 250/560, 573, 574, 222.2

[56] References Cited

U.S. PATENT DOCUMENTS

| | | | |
|---|---|---|---|
| 3,695,765 | 10/1972 | Bol et al. | 356/102 |
| 3,710,933 | 1/1973 | Fulwyler et al. | 356/39 |
| 4,139,303 | 2/1979 | Carlson et al. | 356/39 |
| 4,178,103 | 12/1979 | Wallace | 356/336 |
| 4,260,258 | 4/1981 | Rose et al. | 356/335 |
| 4,329,052 | 5/1982 | Colombo et al. | 356/335 |
| 4,329,053 | 5/1982 | Fymat | 356/336 |
| 4,361,403 | 11/1982 | Loos | 356/336 |
| 4,457,624 | 7/1984 | Goldberg et al. | 356/336 |
| 4,497,577 | 2/1985 | Sato et al. | 356/336 |
| 4,529,309 | 7/1985 | Pettersson et al. | 356/335 |
| 4,540,283 | 9/1985 | Bachalo | 356/336 |
| 4,735,504 | 4/1988 | Tycko | 356/336 |
| 4,771,181 | 9/1988 | Hayashi | 250/560 |
| 4,776,697 | 10/1988 | Kamrat | 356/336 |
| 4,842,406 | 6/1989 | VonBargen | 356/336 |
| 4,893,929 | 1/1990 | Miyamoto | 356/336 |
| 4,940,326 | 7/1990 | Tatsuno | 356/336 |
| 4,953,978 | 9/1990 | Bott et al. | 356/336 |
| 4,983,040 | 1/1991 | Chu et al. | 356/338 |
| 5,090,808 | 2/1992 | Ishikawa et al. | 356/336 |

FOREIGN PATENT DOCUMENTS

| | | | |
|---|---|---|---|
| 0273431 | 11/1987 | Japan | 356/335 |
| 63-311144 | 12/1988 | Japan . | |

*Primary Examiner*—Hoa Q. Pham
*Attorney, Agent, or Firm*—J. T. Hoppe

[57] ABSTRACT

An apparatus and method are disclosed which allow the size of a particle suspended in a medium to be determined virtually independent of the materials' refractive index. The apparatus includes a light source, a sample holder, a detector and a spatial filter. The method of the invention comprises passing the medium containing the particle through a beam of collimated light so that the light which contacts the particle will be scattered; deterring the light which was scattered by the particles from being detected, detecting the light which was not scattered by the particle; and determining the size of the particle from the decrease in the light intensity incident on the detector.

10 Claims, 2 Drawing Sheets

APPARATUS AND METHOD FOR USING LIGHT SCATTERING TO DETERMINE THE SIZE OF PARTICLES VIRTUALLY INDEPENDENT OF REFRACTIVE INDEX This invention relates to an apparatus and method for using light scattering to measure the size of particles suspended in a fluid medium.

BACKGROUND OF THE INVENTION

Particle size analysis through means of light obscuration or light extinction is often the preferred method of size determination, for several reasons. Light obscuration offers particle size distribution measurement as well as mean size assignment. Particle size measurements by light obscuration exhibit good reproducibility, relatively quick analyses, applicability in a wide range of fluids, and can be used in the analysis of particles in the size range of approximately 1 to 2500 $\mu$m. Accordingly, light obscuration is a widely practiced technique for particle size determinations.

Particle sizing by light obscuration is based on the principle of light scattering. Generally, a light source is employed which delivers a collimated beam of light with a uniform intensity distribution to a photodetector. A flow cell allows particles suspended in a fluid medium to intercept the collimated beam of light. The fluid that carries the particles through the flow cell can be either a gas or a liquid. The portion of the collimated beam that intersects the fluid within the flow cell is referred to as the measurement volume. The amount of light incident on the detector in the absence of particles is constant and known. As a particle passes through the measurement volume, the particle will scatter light, resulting in a decrease of light incident on the detector. For any given particle and fluid medium composition, large particles will scatter more light than small particles. Accordingly, the reduction in the amount of light incident on the detector, observed as a particle passes through the measurement volume, is used to determine the size of the particle.

While this technique has proven to be very valuable, certain deficiencies still exist. One of these deficiencies is that the accuracy of the commercial sensors is dependent upon the relative refractive index of the particles and the fluid medium.

It is therefore an objective of the current invention to provide an instrument and a method for determining the size of particles suspended in a medium wherein the determination is less dependent of the relative refractive index of the materials.

SUMMARY OF THE INVENTION

In accordance with the present invention, an apparatus and method are provided for determining the size of particles suspended in a medium. The apparatus includes a means for producing a beam of collimated light, a means for exposing the particles to the collimated beam of light, thereby scattering the light, a detector, and a means for deterring light which was scattered by the particles from reaching the detector.

The method of the invention comprises passing the medium containing the particles through a beam of collimated light, so that the light which contacts the particles will be scattered; determining the reduction of light transmitted to a detector; deterring the light which was scattered by the particles from being detected; and determining the size of the particle from the amount of light incident on the detector.

For a more complete understanding of the invention, reference should be made to the Detailed Description of the Invention, which makes reference to the following drawings:

DETAILED DESCRIPTION OF THE INVENTION

Figure 1:
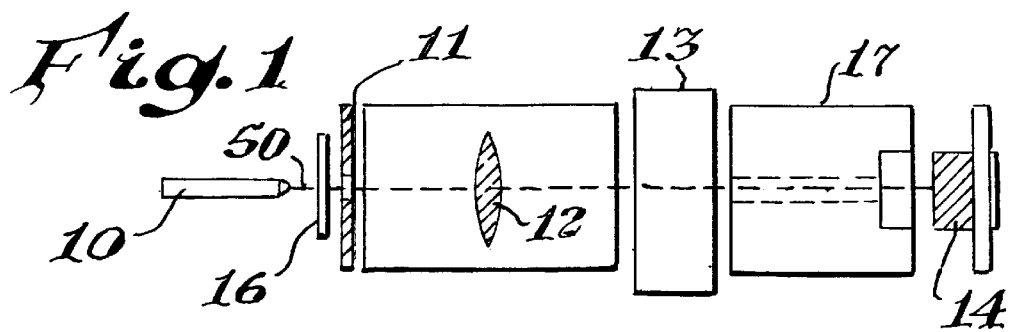
FIG. 1 is a schematic diagram of one embodiment of the apparatus invention, showing a detector extender inserted into a conventional particle sizing by light obscuration instrument.

In general, current instruments which are used to determine the size of a particle suspended in a medium using the technique of light obscuration consist of many of the elements shown in FIG. 1. This includes a light source 10 which delivers a collimated light beam of uniform intensity; a flow cell 13, which allows the particles to be exposed to the collimated light; and a detector means 14 for measuring the intensity of the beam after passing through the flow cell 13. The components are aligned along an optical axis 50, such that light will travel along the axis 50 from the light source 10 through the flow cell 13 to the detector 14. As a particle flows through the flow cell it will scatter the collimated light and the change in light intensity will be measured by a suitable detection means 14.

While collimated light is preferred and is used by current instruments, divergent or convergent light can also be used with the invention in its broadest aspects. Collimated light can be achieved using a diffuser 16/pinhole 11 assembly as shown in FIG. 1. The size of the pinhole 11 directly impacts the degree of collimation that can be obtained and the intensity of light that is imparted on the flow cell. The quality of the diffuser 16 impacts how uniform the light intensity is in the collimated beam. A laser beam is another well known source of collimated light. The collimation of the light should be aligned such that it is parallel to the optic axis 50 of the instrument The detector 14 is positioned to collect all of the unscattered rays which pass through the flow cell 13. Each detector 14 also has a unique angle of light collection (termed the collection angle), which is determined by the geometry of the detector 14 and any optical components placed between the flow cell 13 and the detector 14. The collection angle will determine how much of the light scattered by a particle will be collected by the detector 14. The lower the collection angle the less scattered light will be detected.

One approach to modeling the light scattering is to combine the effects of reflection, refraction, and diffraction. These three light loss mechanisms could potentially contribute to light obscuration particle sizing artifacts. Of these three, diffraction can be ignored, as the scattering due to diffraction is confined to very small scattering angles, and hence the bulk of the diffracted light will be collected by the detector.

Figure 2:
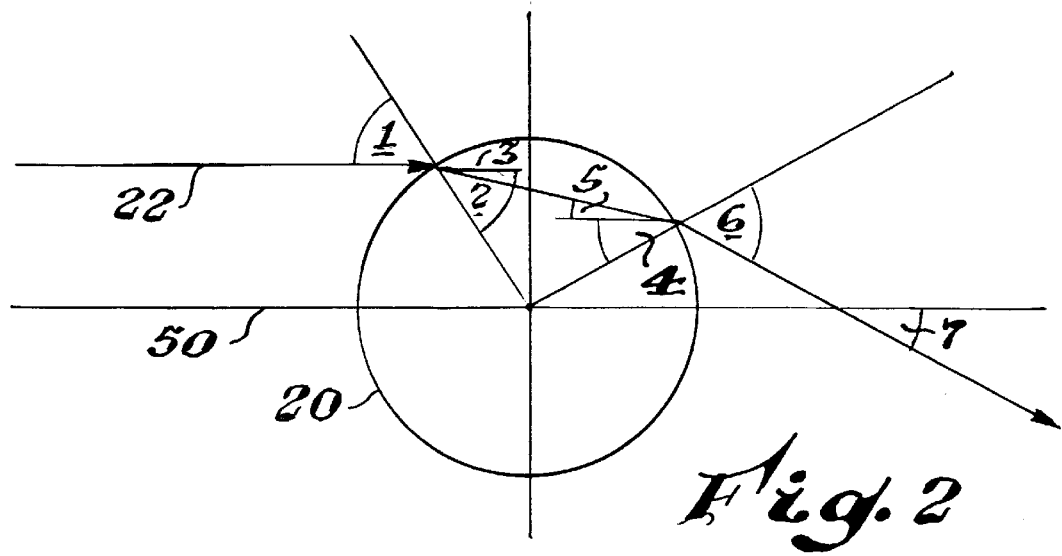
FIG. 2 is a diagram showing how a ray of light which strikes a particle parallel to the optic axis will be altered by the particle.

By ignoring the loss of light due to diffraction, the response of the sensor can be described in terms of Snell's law of refraction and Fresnel's laws of reflection. These principles are more fully described in F. A. Jenkins, H. E. White, *Fundamentals of Optics*, 4th ed., McGraw-Hill (1976), herein incorporated by reference. FIG. 2 shows the geometry that has been used to describe the interaction of the collimated incident light ray 22 with a particle 20 in the flow cell 13. Angle 1 can be calculated from the position of the incident light ray 22 on the particle 20. Given angle 1 and the refractive indexes of the materials, angles 2–7 can be calculated using Snell's law. The attenuation of the transmitted ray at each of the points of interaction on the surface of the particle 20 can be calculated using Fresnel's laws.

Angle 7 in FIG. 2 is the critical angle for particle sizing by light obscuration. For any given ray, when angle 7 is greater than the collection angle of the particular detector 14 with its accompanying receiving optics (if any), the light will not be collected by the detector. When the light is not detected, the transmittance value will drop. If angle 7 is less than the collection angle, however, the light will be collected by the detector 14, just as if the light had passed through the sample cell 13 without contacting a particle 20. The amount of light collected by the detector 14 can be determined for the full set of incident rays parallel to the optic axis 50. The transmittance values thus determined can then be used to determine the amount of light which is intercepted by the entire surface of the particle, but is still collected by the detector 14. It is this light which causes sizing errors in light obscuration particle sizers. Angle 7 is dependent upon the relative refractive index of the materials, which is determined by dividing the refractive index of the particle 20 by the refractive index of the suspending medium. As the relative refractive index approaches 1, angle 7 approaches zero. Thus, as the relative refractive index approaches 1, more and more light which contacted a particle 20 will nevertheless be collected by a detector 14 having a given collection angle.

Understanding the relationship between relative refractive index and the amount of light collected by the detector, allows the particle sizing instrument to be optimized. Smaller collection angles will produce more accurate results but typically require more expensive components or more space. When the relative refractive index of the materials to be studied approaches 1, however, smaller collection angles are required for acceptable results. The present invention uses a spatial filter to reduce the collection angle of the detector. For the purposes of this invention, a spatial filter is defined as anything which is designed to eliminate light that was scattered by a particle from reaching the detector.

Figure 4:
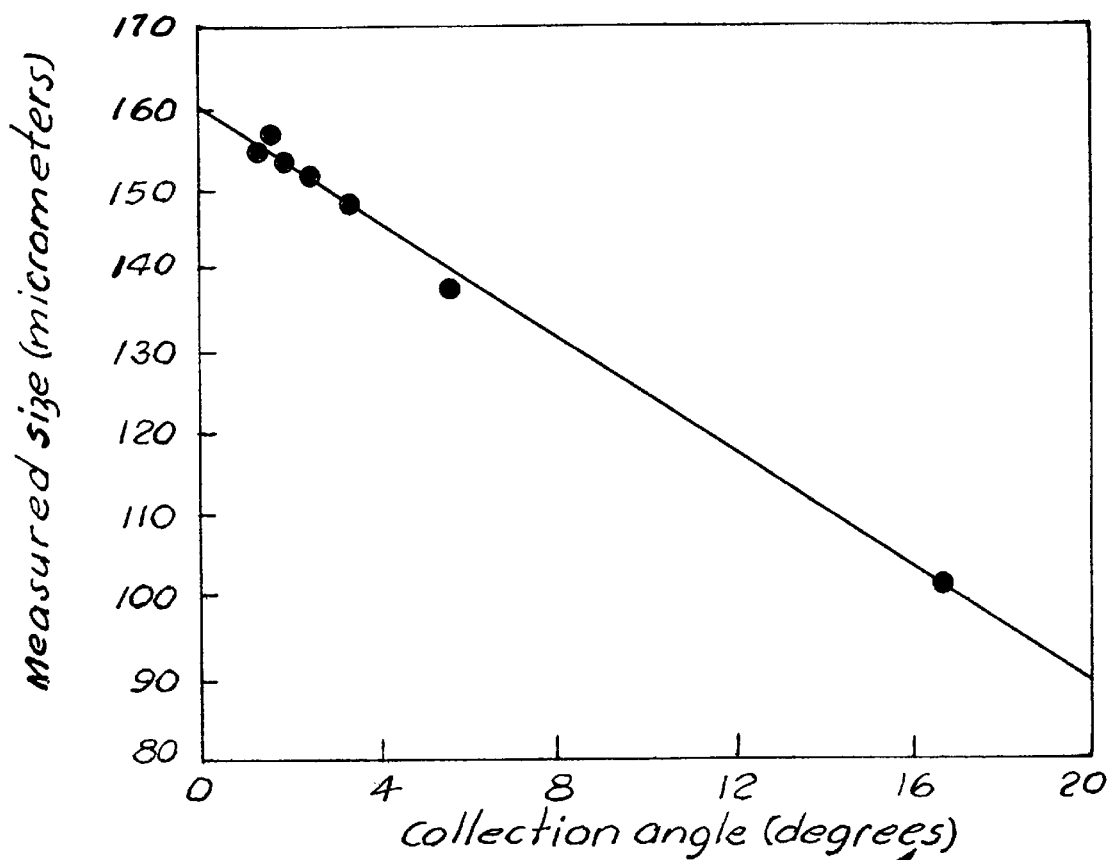
FIG. 4 is a graph demonstrating the dependence of measured size on collection angle for a system with a particular relative refractive index.

An acceptable collection angle (and hence the proper spatial filter) can be determined by varying the collection angle of the detector. FIG. 4 represents typical results obtained by varying the collection angle of an instrument, while keeping the relative refractive index of the materials constant. The collection angle should be chosen so that it is in the region of the graph where accuracy is acceptable for the particular application. As seen from the graph, accuracy improves as the collection angle approaches zero. As the graph is linear, it should also be understood that the measured value for a collection angle of zero degrees can be determined from extrapolation from two collection angles. Furthermore, the slope of the line is related to the relative refractive index of the materials.

The instrument should be optimized to meet the needs of a particular analysis. It is preferred, however, that the collection angle be less than 5°, more preferably less than 3°, still more preferably less than 2°, even more preferably less than 1.5°, and most preferably 1° or less. It should be understood, however, that the collection angle must not be so small that light which passes through the measurement volume is not detected. In other words, the collection angle cannot be zero, otherwise insufficient light will reach the detector.

Figure 3:
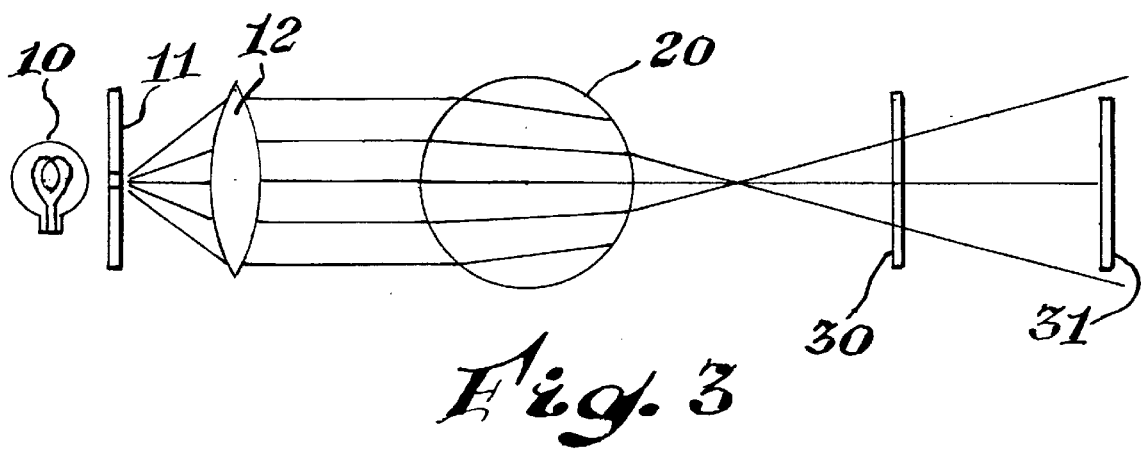
FIG. 3 is a diagram which demonstrates how moving the detector away from the flow cell decreases the light collection angle.

A spatial filter for reducing the collection angle can take several forms, some of which will be described below: one way, as shown in FIG. 1, is to simply increase the distance between the flow cell 13 and the detector 14. Moving the detector further from the particle 20 effectively decreases the collection angle of the detector. This is clearly shown in FIG. 3 which depicts several collimated rays of light striking a particle 20 in the flow cell 13, and the resulting scattering of the light. Detector 30, which is closer to the particle 20, will collect all of the scattered rays, whereas detector 31, which is placed further from the particle 20, will not. As seen in FIG. 1, a detector extender 17 is placed between the flow cell and the detector. This modification decreases the collection angle of the detector and additionally blocks ambient light from reaching the detector.

This collection angle geometry can be represented mathematically. The light collection angle is given by the following equation:

$$\text{detector collection angle} = \tan^{-1}(y/x)$$

where x is the distance from the flow cell 13 to the detector 14, and y is the radius of the active surface of the detector. Thus, the distance between the flow cell 13 and the detector 14 is approximately inversely proportional to the collection angle. Therefore, as x gets larger, the collection angle gets smaller. The length of the detector extender 17, determines x and can be adjusted to give the desired collection angle.

A second way to reduce the collection angle is to simply reduce the size of the portion of the detector which collects the light using a mask or a detector with a smaller active surface. As seen from the equation for the detector collection angle given above, the collection angle can be reduced either by increasing x or decreasing y. However, it should be noted that y should not be reduced to a value less than the height of the light beam at the point where the mask is placed or at the surface of the detector if no mask is used, otherwise trajectory dependent sizing errors will occur. While both of these ways reduce the collection angle, they both theoretically allow some rays which were scattered by the particle 20 to reach the detector.

Figure 5:
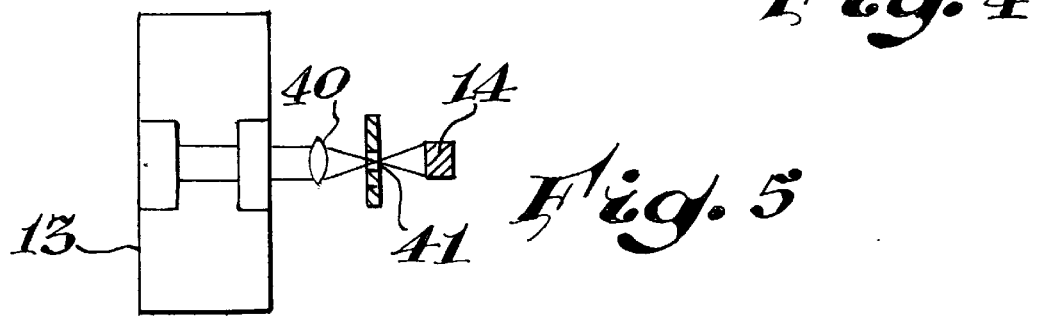
FIG. 5 is a schematic diagram of another embodiment of the invention utilizing a lens and a pinhole.
Figure 6:
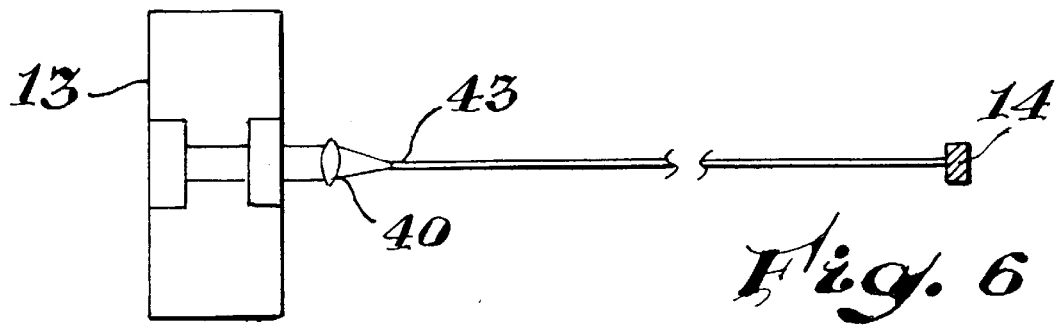
FIG. 6 is a schematic diagram of a third embodiment of the invention utilizing a lens and a fiber optic cable.

An alternate way of reducing the collection angle, is to use a lens 40 and a spatial filter placed in between the flow cell 13 and the detector 14, as shown in FIGS. 5 and 6. The lens will focus all rays parallel to the optic axis 50 which strike the lens, so that the rays will be directed to a focal point. Any rays which have been scattered by a particle 20 such that they are no longer parallel to the optical axis of the system, will not be directed to the focal point. Thus, if all light rays which do not pass through this focal point are excluded, using a suitable spatial filter, then only rays which have not been scattered off-axis by a particle will be detected. The lens alone will not create the desired result of eliminating the unwanted scattered light. The lens is simply used to facilitate the use of a spatial filter.

The spatial filter can be a pinhole 41 in a thin piece of metal, as shown in FIG. 5. The diameter of the pinhole will define the collection angle. Alternatively, a fiber optic cable 43 can act as the spatial filter, as shown in FIG. 6. The fiber optic cable 43 can be placed at the focal point so that only light rays which pass through the focal point will be collected by the fiber optic cable 43. Like the pinhole 41 in FIG. 5, the diameter of the fiber optic cable should be selected so as to optimize the collection angle. Another alternative is to provide a detector 14 with a limited active collection area. In that case, the active collection area of the detector 14 would be located at the focal point of the lens, and be as small as needed to define the optimum collection angle. It should be noted that smaller collection angles as determined by the size of the spatial filter components (e.g. pinhole, fiber optic cables, or active collection areas) enable more of the scattered light to be excluded.

It should be realized by one of ordinary skill in the art that the invention is not limited to the exact configuration or methods illustrated above, but that various changes and modifications may be made without departing from the spirit and scope of the invention as described within the following claims.

What is claimed is:

1. In an apparatus for determining the size of particles suspended in a medium, said apparatus being of the type having a means for producing a beam of light; a means for exposing the particles to the beam of light, whereby the light which contacts the particles is scattered; and a means for detecting the light over a given collection angle after it has passed through the means for exposing the particles to the beam of light, the improvement comprising: a spatial filter for reducing the collection angle to less than about three degrees, wherein the spatial filter includes a detector extender located between the means for exposing the particles to the beam of light and the light detection means, wherein the detector extender blocks ambient light and is of sufficient length to deter light which was scattered by the particles from reaching the detector.

2. In an apparatus for determining the size of particles suspended in a medium, said apparatus being of the type having a means for producing a beam of light; a means for exposing the particles to the beam of light, whereby the light which contacts the particles is scattered; and a means for detecting the light over a given collection angle after it has passed through the means for exposing the particles to the beam of light, the improvement comprising: a spatial filter for reducing the collection angle to less than about three degrees wherein the means for producing a beam of light is capable of producing a collimated beam of light such that the rays of light are all generally parallel to an optical axis, wherein the spatial filter is used in conjunction with a lens placed on the optical axis of the collimated light, the lens being located between the detecting means and the means for exposing the particles to the collimated light, wherein the lens will focus all rays of light which are parallel to the optic axis at a focal point and wherein the spatial filter comprises a fiber optic cable having a diameter equal to the diameter of the beam of light rays at the focal point, said fiber optic cable being located at the focal point of the lens, such that only the rays of light which pass through the focal point will be directed into the fiber optic cable.

3. A method for determining the size of a particle suspended in a medium comprising:

(a) passing the medium containing the particle through a beam of light, so that the light which contacts the particle will be scattered;

(b) detecting the light which was not scattered by the particle;

(c) deterring the light which was scattered by the particles from being detected, such that only light which falls within a collection angle of 3° or less is detected; and (d) determining the size of the particle from the decrease in light detected as the particle passed through the beam of light.

4. The method of claim 3 wherein the beam of light is collimated before passing the medium containing the particle through it.

5. The method of claim 4 wherein step (c) comprises: passing the light through a lens having an optic axis which is aligned with the collimated beam, so that the lens focuses all light rays which are parallel to its optic axis at a focal point, the lens being located after exposing the particles to the light.

6. The method of claim 5 further comprising passing the light through a spatial filter located at the focal point, the spatial filter being configured so that only light which passes through the focal point will be allowed to pass.

7. The method of claim 5 further comprising directing the light which passes through the focal point into a fiber optic cable.

8. The method of claim 3 wherein only light which falls within a collection angle of 2° or less is detected.

9. The method of claim 3 wherein only light which falls within a collection angle of 1.5° or less is detected.

10. The method of claim 3 wherein only light which falls within a collection angle of 1° or less is detected.

* * * * *